US00PP14125P29

(12) United States Plant Patent
Miyazaki

(10) Patent No.: US PP14,125 P2
(45) Date of Patent: Sep. 2, 2003

(54) PETUNIA PLANT NAMED 'SUNROVE'

(75) Inventor: Kiyoshi Miyazaki, Hikone (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 10/067,802

(22) Filed: Feb. 8, 2002

(51) Int. Cl.[7] ..... A01H 5/00
(52) U.S. Cl. ..... Plt./356
(58) Field of Search ..... Plt./356

(56) References Cited

U.S. PATENT DOCUMENTS

| | | | |
|---|---|---|---|
| PP6,899 | P | 7/1989 | Tsuda et al. |
| PP6,914 | P | 7/1989 | Tsuda et al. |
| PP6,915 | P | 7/1989 | Tsuda et al. |
| PP8,489 | P | 12/1993 | Hirabayashi et al. |
| PP8,768 | P | 6/1994 | Hirabayashi et al. |
| PP9,322 | P | 10/1995 | Tachibana et al. |
| PP9,341 | P | 10/1995 | Tachibana et al. |
| PP9,342 | P | 10/1995 | Sakazaki et al. |
| PP9,556 | P | 5/1996 | Tachibana et al. |
| PP9,557 | P | 5/1996 | Suzuki et al. |
| PP9,754 | P | 12/1996 | Suzuki et al. |
| PP10,045 | P | 9/1997 | Rother |
| PP10,278 | P | 3/1998 | Murakami |
| PP10,279 | P | 3/1998 | Murakami |
| PP10,287 | P | 3/1998 | Murakami |
| PP10,310 | P | 3/1998 | Sakazaki |
| PP10,330 | P | 4/1998 | Sakazaki |
| PP10,355 | P | 4/1998 | Murakami |
| PP10,904 | P | 5/1999 | Hansson |
| PP11,006 | P | 7/1999 | Danziger |
| PP11,352 | P | 4/2000 | Murakami |
| PP11,558 | P | 10/2000 | Murakami |
| PP12,101 | P2 | 9/2001 | Sakazaki |

*Primary Examiner*—Bruce R. Campell
*Assistant Examiner*—Anne Marie Grünberg
(74) *Attorney, Agent, or Firm*—Burns, Doane, Swecker & Mathis, L.L.P.

(57) ABSTRACT

Disclosed herein is a new and distinct variety of Petunia plant having a decumbent habit and long stems. The Petunia plant has abundant branching, and great profusion of blooms, the whole plant remaining in bloom for a considerable period of time. The flowers are single and medium size, the petals having a light purplish pink ground color with a vivid reddish purple vein pattern. The bottom color of the corolla throat is brilliant purple and the outside of the corolla tube is very pale violet. The plant exhibits high resistance to rain, heat and disease.

3 Drawing Sheets

Botanical/commercial classification: Petunia hybrida/Petunia Plant.

Varietal denomination: cv. 'Sunrove'.

BACKGROUND OF THE VARIETY

The Petunia is a very popular plant that is used for flower bedding and potting in the summer season. There are only a few Petunia varieties which do not have an upright growth habit and which have a high resistance to rain, heat, and diseases. The Petunia plants of the REVOLUTION Series [i.e., 'Revolution Purple pink' (U.S. Plant Pat. No. 6,915), 'Revolution Brilliant pink' (U.S. Plant Pat. No. 6,914), 'Revolution Brilliant pink-mini' (U.S. Plant Pat. No. 6,899), 'Revolution Bluevein' (U.S. Plant Pat. No. 9,322), and 'Revolution Pinkvein' (U.S. Plant Pat. No. 9,341)] are decumbent type plants having long stems, a lower plant height, abundant branching, and a high resistance to heat, rain and disease. However, there are only a few Petunia varieties having a great profusion of flowers, pastel-colored with vein pattern flower petals and a high resistance to rain, heat, and diseases. Accordingly, this invention is aimed at obtaining a new variety having light purplish pink colored petals with a vivid reddish purple vein pattern, together with the above features.

The new variety of Petunia plant according to this invention originated from crossing a seedling named '6Pt-160-1' (♀) (non-patented in the United States), and a wild type Petunia plant named '1792' (♂) (non-patented in the United States).

The '6Pt-160-1' variety was a seedling obtained from the 'Falcon Plum' variety (non-patented in the United States). The '1792' variety (non-patented in the United States) is a decumbent, wild type Petunia plant native to Brazil. In April 1997, the crossing and the '1792' as pollen parent was conducted. In January 1998, 120 seedlings were obtained from such crossing. These seedlings were grown in pots and were evaluated and 2 seedlings were selected. One of these subsequently was selected in view of its decumbent growth habit and light purplish pink colored petals with a vivid reddish purple vein pattern. That seedling was propagated by the use of cuttings in July 1998 in Shiga-Ken, Japan, and a trial was carried out by flower potting and bedding beginning in March 1999. The botanical characteristics of that plant were then examined using a similar variety 'Revolution Pinkvein' for comparison. As a result, it was concluded that this Petunia plant is distinguishable from other varieties whose existence is known, and uniform and stable in its characteristics. Then, the new variety of Petunia plant was named 'Sunrove'.

In the following description, the color-coding is in accordance with The R.H.S. Colour Chart of The Royal Horticultural Society, London, England (hereafter designated R.H.S.). A color chart based on The Japan Color Standard for Horticultural Plants (J.H.S. Color Chart) is also added for reference.

The female parent used in the crossing of 'Sunrove' named '6Pt-160-1' has an erect habit while that of the new variety is decumbent. The branching is less than the new variety. The petals are light purplish pink (R.H.S. 73C, J.H.S. 8903) with strong reddish purple (R.H.S. 72B, J.H.S. 9208) vein. The bottom color of the corolla throat is moderate reddish purple (R.H.S. 79C, J.H.S. 8913), and the outside color of the corolla tube is pale purple (R.H.S. 85D, J.H.S. 8914).

The main botanical characteristics of the '6Pt-160-1' parent are as follows:

Plant:
- *Growth habit.*—Erect.
- *Plant height.*—Approximately 18 cm.
- *Spreading area of plant.*—Small.
- *Blooming period.*—April to July in the southern Kanto area, Japan.

Stem:
- *Length.*—Approximately 13.5 cm.
- *Thickness.*—Main stem approximately 1.8 mm.
- *Pubescence.*—Normal.
- *Branching.*—Medium.
- *Length of internode.*—Approximately 1.8 cm.
- *Color.*—Strong yellow green (R.H.S. 137C, J.H.S. 3512).

Leaf:
- *Whole shape.*—Elliptic. The apex shape is acute, and the base shape is attenuate.
- *Length.*—Approximately 8.0 cm.
- *Width.*—Approximately 3.8 cm.
- *Color.*—Upper-side color is moderate yellow green (R.H.S. 137C, J.H.S. 3712). Bottom-side color is moderate yellow green (R.H.S. 147B, J.H.S. 3513).
- *Pubescence.*—Normal.

Flower:
- *Facing direction.*—Upward.
- *Type.*—Single.
- *Shape.*—Funnel-shape, with five lobes.
- *Shape of petal tip.*—Round.
- *Lobation.*—Shallow.
- *Waving of petal.*—Weak.
- *Diameter.*—Approximately 5.8 cm.
- *Color.*—Petal; Light purplish pink (R.H.S. 73C, J.H.S. 8903) with strong reddish purple (R.H.S. 72B, J.H.S. 9208) vein. The bottom color of the corolla throat is moderate reddish purple (R.H.S. 79C, J.H.S. 8913). The outside color of the corolla tube is pale purple (R.H.S. 85D, J.H.S. 8914).
- *Reproductive organs.*—1 normal pistil and 5 normal stamens. The color of pistil is strong yellow green (R.H.S. 144B, J.H.S. 3512). The color of stamen is light olive gray (R.H.S. 197C, J.H.S. 3112).
- *Peduncle.*—Approximately 1.5 mm in thickness, and approximately 1.5 cm in length.
- *Physiological and ecological characteristics.*—Moderate resistance to cold, heat, diseases and pests. Low resistance to rain.

The pollen parent '1792' used in the crossing of 'Sunrove' variety was a wild type Petunia plant native to Brazil. The Petunia plant '1792' has a decumbent habit with long stems and much branching. The leaf is very small and without a petiole. It has very small single flower, and the petals having yellowish white (R.H.S. 158D, J.H.S. 2502) coloration with a strong reddish purple (R.H.S. 72B, J.H.S. 9208) vein.

The main botanical characteristics of variety 1792 parent are as follows:

Plant:
- *Growth habit.*—Decumbent.
- *Plant height.*—Approximately 5.5 cm.
- *Spreading area of plant.*—Large.
- *Blooming period.*—May to August in the southern Kanto area, Japan.

Stem:
- *Length.*—Approximately 15.0 cm.
- *Thickness.*—Approximately 1.3 mm.
- *Pubescence.*—Normal.
- *Branching.*—Much.
- *Length of internode.*—Approximately 1.0 cm.
- *Color.*—Strong yellow green (R.H.S. 144B, J.H.S. 3512).

Leaf:
- *Whole shape.*—Elliptic. The apex shape is acute, and the base shape is attenuate.
- *Length.*—Approximately 2.5 cm.
- *Width.*—Approximately 1.5 cm.
- *Color.*—Upper-side color is strong yellow green (R.H.S. 143A, J.H.S. 3711). Bottom-side color is moderate yellow green (R.H.S. 147B, J.H.S. 3513).
- *Pubescence.*—Sparse.

Flower:
- *Facing direction.*—Horizontal.
- *Type.*—Single.
- *Shape.*—Funnel-shape, with five lobes.
- *Shape of petal chip.*—Round.
- *Lobation.*—Shallow.
- *Waving of petal.*—Weak.
- *Diameter.*—Approximately 4.3 cm.
- *Color.*—Petal; Yellowish White (R.H.S. 158D, J.H.S. 2502) with strong reddish purple (R.H.S. 72B, J.H.S. 9208) vein. The bottom color of the corolla throat is greenish white (R.H.S. 155C, J.H.S. 3501). The outside color of the corolla tube is brilliant yellow green (R.H.S. 145B, J.H.S. 3504).
- *Reproductive organs.*—1 normal pistil and 5 normal stamens. The color of pistil is strong yellow green (R.H.S. 144B, J.H.S. 3512). The color of stamen is light olive gray (R.H.S. 197C, J.H.S. 3112).
- *Peduncle.*—Approximately 1.0 mm in thickness, and approximately 2.4 cm in length.
- *Physiological and ecological characteristics.*—Moderate resistance to cold and pests. Strong resistance to rain, heat and diseases.

The main botanical characteristics of a similar variety 'Revolution Pinkvein' variety (U.S. Plant Pat. No. 9,341) for comparison are as follows:

Plant:
- *Growth habit.*—Decumbent. The stems hang down when potted in a hanging pot.
- *Plant height.*—Approximately 15–25 cm.
- *Spreading area of plant.*—Large.
- *Blooming period.*—April to September in the southern Kanto area, Japan.

Stem:
- *Length.*—Approximately 60–80 cm.
- *Thickness.*—Approximately 3.0–4.0 mm.
- *Pubescence.*—Medium.
- *Branching.*—Very abundant (primary), abundant (secondary).
- *Length of internode.*—Approximately 2.0–4.0 cm.

*Color.*—Strong yellow green (R.H.S. 144B, J.H.S. 3512).

Leaf:

*Leaf attaching angle.*—Horizontal.

*Whole shape.*—Oval. Length. Approximately 4.0–5.0 cm.

*Width.*—Approximately 2.0–3.5 cm.

*Color.*—Upper-side color is moderate olive green (R.H.S. 146A, J.H.S. 3508). Bottom-side color is moderate yellow green (R.H.S. 147B, J.H.S. 3513).

*Pubescence.*—Medium.

Flower:

*Facing direction.*—Obliquely upward.

*Type.*—Single.

*Shape.*—Funnel-shape, with five lobes.

*Shape of petal tip.*—Round.

*Lobation.*—Shallow.

*Waving of petal.*—Weak.

*Diameter.*—Approximately 3.5–5.5 cm.

*Color.*—Petal is bi-colored with a vein pattern. The ground color is deep purplish pink (R.H.S. 70C, J.H.S. 9213) and pattern color is strong reddish purple (R.H.S. 72A, J.H.S. 9209) to dark reddish purple (R.H.S. 79A, J.H.S. 9218). The bottom throat inside portion of the corolla is a dark reddish purple color (R.H.S. 79A, J.H.S. 9213).

*Reproductive organs.*—1 normal pistil and 5 normal stamens. The pistil color is strong yellow green (R.H.S. 144B, J.H.S. 3512). The stamen color is light olive gray (R.H.S. 197C, J.H.S. 3112).

*Peduncle.*—Approximately 2.0–2.5 mm in thickness, and approximately 0.2–0.3 cm in length.

*Physiological and ecological characteristics.*—High resistance to cold, rain and heat. Also high resistance to disease. Moderate resistance to pests.

SUMMARY OF THE NEW VARIETY

The new variety of the petunia plant has a decumbent growth habit, abundant branching and great profusion of blooms with the whole plant remaining in bloom for a considerable period of time. The flowers are single and medium size. The petal color is light purplish pink with vivid reddish purple vein pattern. The plant has a high resistance to rain, heat and diseases.

BRIEF DESCRIPTION OF THE PHOTOGRAPHS

DETAILED DESCRIPTION OF THE NEW VARIETY

Figure 1:
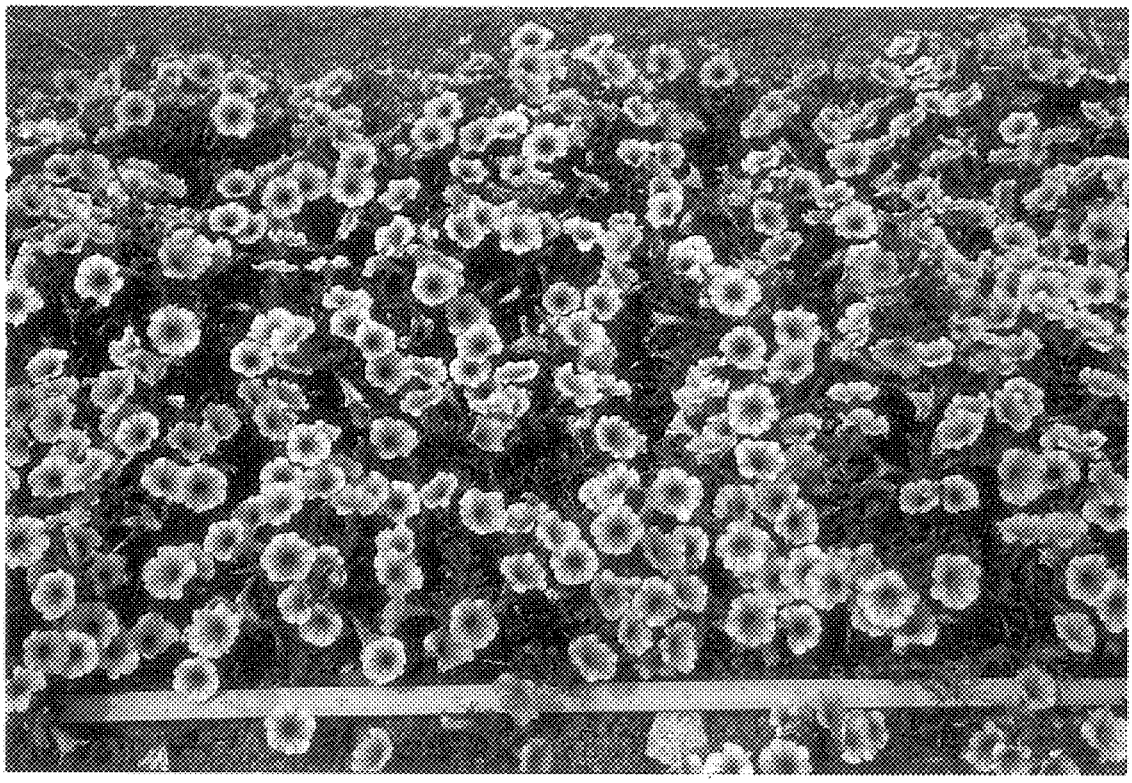
FIG. 1 is a photograph showing a partial view of the new variety of the Petunia plant 'Sunrove' while growing in the ground.
Figure 2:
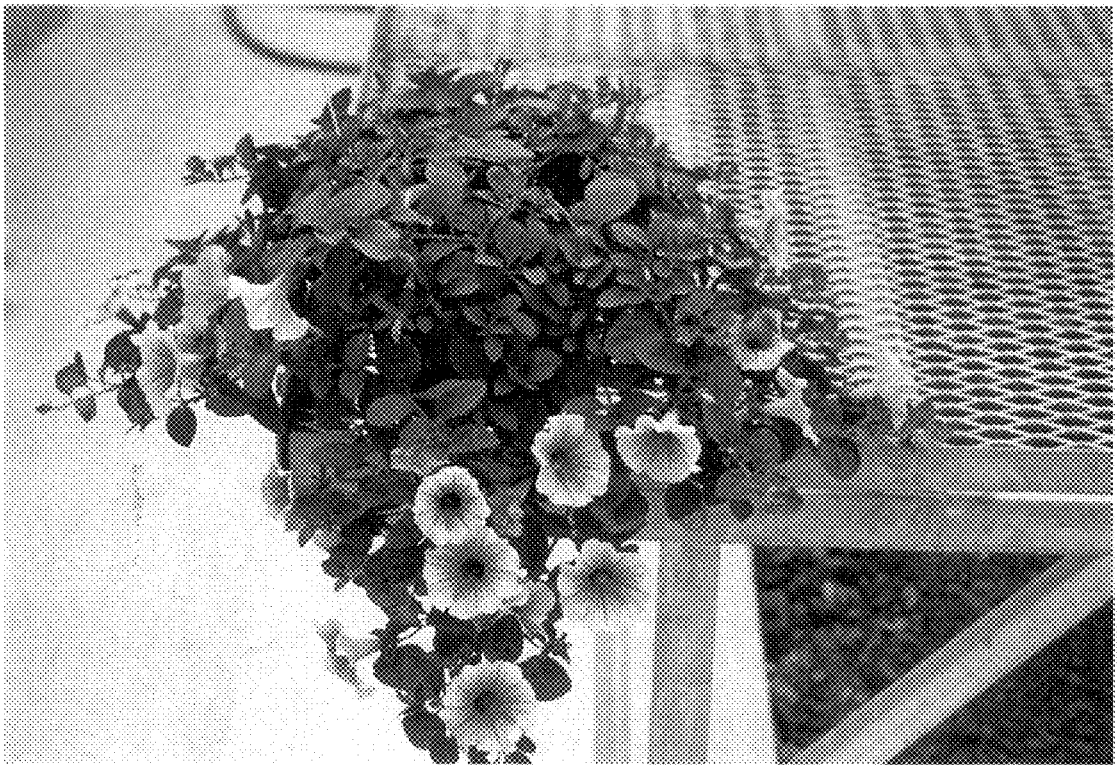
FIG. 2 is a photograph showing a view of the variety of the Petunia plant 'Sunrove' while growing in a flower pot.
Figure 3:
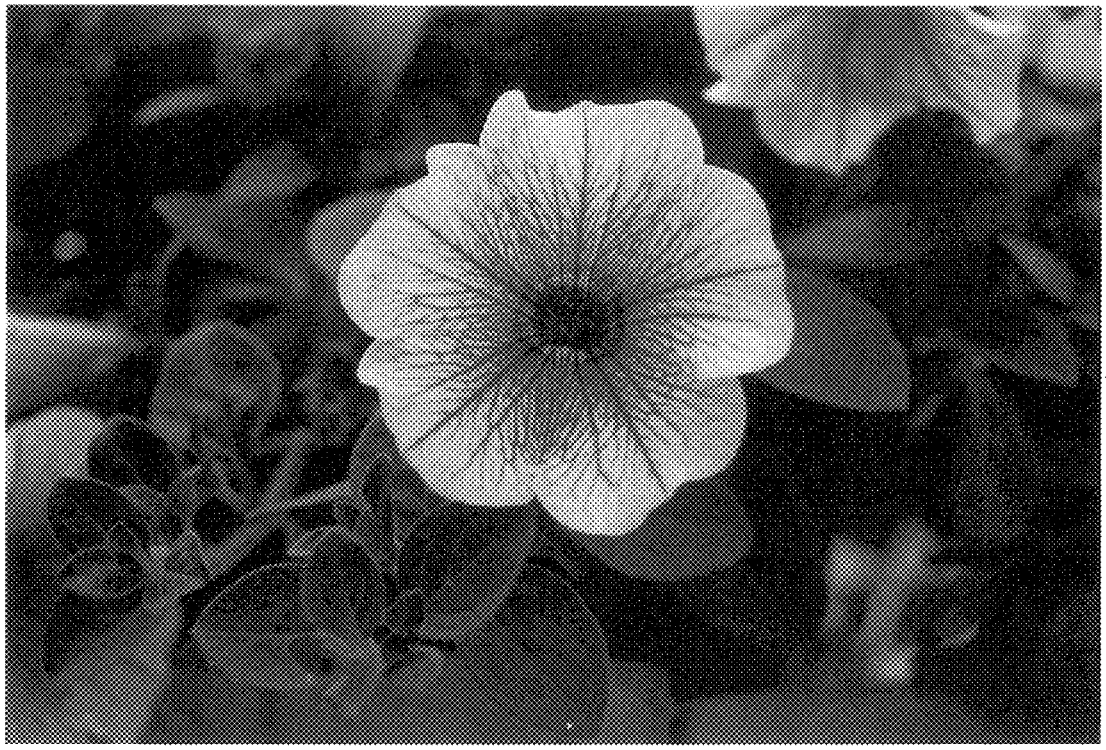
FIG. 3 is a photograph of flowers and leaves of the new variety of the Petunia plant 'Sunrove'.

The botanical characteristics of the new and distinct variety of Petunia plant named 'Sunrove' are as follows.

Plant:

*Growth habit.*—Decumbent.

*Plant height.*—Approximately 10.5 cm.

*Spreading area of plant.*—Large.

*Blooming period.*—April to late September in the southern Kanto area, Japan. The plant shape does not change throughout this period. A typical flower commonly lasts approximately 5 days on the plant when experiencing a temperature of approximately 20° C.

Stem:

*Length.*—Approximately 12.0 cm.

*Thickness.*—Approximately 1.8 mm.

*Pubescence.*—Dense.

*Branching.*—Abundant.

*Length of internode.*—Approximately 0.9 cm.

*Color.*—Strong yellow green (R.H.S. 144B, J.H.S. 3512).

Leaf:

*Whole shape.*—Elliptic. The apex shape is acute, and the base shape is attenuate.

*Length.*—Approximately 8.0 cm.

*Width.*—Approximately 4.4 cm.

*Color.*—The upper side color is moderate olive green (R.H.S. 146A, J.H.S. 3508). The bottom side color is moderate yellow green (R.H.S. 147B, J.H.S. 3513).

*Thickness.*—Approximately 0.3 mm.

*Pubescence.*—Medium.

Flower:

*Bud length.*—Approximately 3.4 cm.

*Bud width.*—Approximately 1.2 cm.

*Bud color.*—Pale violet (R.H.S. 92D).

*Facing direction.*—Slanted upward.

*Type.*—Single.

*Shape.*—Funnel-shape, with five lobes.

*Shape of petal tip.*—Round.

*Lobation.*—Shallow.

*Waving of petal.*—Weak.

*Diameter.*—Approximately 5.5 cm.

*Color.*—Petal is light purplish pink (R.H.S. 73C, J.H.S. 8903) with a vivid reddish purple (R.H.S. 74A, J.H.S. 9207) vein. The bottom color of the corolla throat is brilliant purple (R.H.S. 81C, J.H.S. 8604). The outside color of the corolla tube is very pale violet (R.H.S. 92D, J.H.S. 8002).

*Reproductive organs.*—1 normal pistil and 5 normal stamens. The color of the pistil is strong yellow green (R.H.S. 144B, J.H.S. 3512). The color of the stamen is light purple (R.H.S. 85A, J.H.S. 8304).

*Peduncle.*—Approximately 0.7 mm in thickness and approximately 1.7 cm in length. The color of the peduncle is strong yellow green (R.H.S. 144B).

*Fruit.*—Pyramidal in shape with rounded corners, and possesses two chambers. The length of the base commonly is approximately 0.6 cm, and the length from the base to the apex commonly is approximately 0.8 cm. The color of the fruit is strong yellow green (R.H.S. 144C).

*Seeds.*—Substantially round and commonly approximately 0.8 mm in diameter. The color of the seeds is dark grayish brown (R.H.S. 200A).

*Physiological and ecological characteristics.*—High resistance to rain, heat and diseases. Moderate resistance to cold and pests.

This new variety of Petunia plant is most suitable for flower bedding and potting, particularly in hanging pots or planters, and is excellent for use as ground cover. Pinching of old blossoms will enhance the formation of new blossoms.

I claim:

1. A new and distinct variety of Petunia plant, substantially as herein illustrated and described, characterized particularly as to novelty by (A) having a decumbent habit with long stems, (B) abundant branching and great profusion of blooms, the whole bush remaining in bloom for a considerable period of time, (C) flowers are single and medium size, the petals have a light purplish pink ground color with a vivid reddish purple vein pattern, and the bottom color of the corolla throat is brilliant purple and the outside color of corolla tube is very pale violet, and (D) has a high resistance to rain, heat and diseases.

* * * * *